United States Patent [19]

Caruthers et al.

[11] Patent Number: 4,668,777
[45] Date of Patent: * May 26, 1987

[54] PHOSPHORAMIDITE NUCLEOSIDE COMPOUNDS

[75] Inventors: Marvin H. Caruthers, Boulder, Colo.; Serge L. Beaucage, Mountain View, Calif.

[73] Assignee: University Patents, Inc., Westport, Conn.

[*] Notice: The portion of the term of this patent subsequent to Nov. 15, 2000 has been disclaimed.

[21] Appl. No.: 637,927

[22] Filed: Aug. 6, 1984

Related U.S. Application Data

[63] Continuation of Ser. No. 358,589, Mar. 16, 1982, abandoned, which is a continuation-in-part of Ser. No. 248,450, Mar. 27, 1981, Pat. No. 4,415,732.

[51] Int. Cl.$^4$ .............................................. C07H 17/00
[52] U.S. Cl. ........................................ 536/27; 536/28; 536/29
[58] Field of Search ............................. 536/27, 28, 29

[56] References Cited

U.S. PATENT DOCUMENTS 3,534,017  10/1970  Fujimoto et al. ..................... 536/29

OTHER PUBLICATIONS

Gatinskaya et al., *Chemical Abstracts*, vol. 79, 1973, p. 351, Abstract No. 146775j.

Matteucci et al., *J. of Am. Chem. Soc.*, vol. 103, No. 11, 1981, pp. 3185–3191.

Beaucage et al., *Tetrahedron Letters*, vol. 22, No. 20, pp. 1859–1862, 1981.

*Primary Examiner*—Johnnie R. Brown
*Assistant Examiner*—Elli Peselev
*Attorney, Agent, or Firm*—George M. Yahwak

[57] ABSTRACT

A new class of nucleoside phosphoramidites which are relatively stable to permit isolation thereof and storage at room temperature. The phosphoramidites are derivatives of saturated secondary amines.

25 Claims, No Drawings

PHOSPHORAMIDITE NUCLEOSIDE COMPOUNDS

The inventions described herein were made in the course of work under a grant or award from the Department of Health, Education and Welfare.

CROSS REFERENCE TO RELATED APPLICATIONS

This application is a continuation of U.S. Ser. No. 358,589 filed Mar. 16, 1982, now abandoned which is a continuation-in-part of U.S. Ser. No. 248,450 filed Mar. 27, 1981, now U.S. Pat. No. 4,415,732.

This invention relates to new and useful Phosphorus compounds which are particularly useful in the production of oligonucleotides.

BACKGROUND OF THE INVENTION

1. Field of the Invention

The present invention relates to new and useful phosphoramidites which are intermediates for polynucleotide synthesis, as well as the improved process for production of oligonucleotides from which polynucleotides are prepared.

2. Description of the Prior Art

Numerous attempts have been made to develop a successful methodology for synthesizing sequence defined oligonucleotides. However, the stepwise synthesis of polynucleotides, and specifically oligonucleotides still remains a difficult and time consuming task, often with low yields. One prior art technique has included the use of organic polymers as supports during polynucleotide synthesis. Classically the major problems with polymer supported synthesis strategies has been inherent in the nature of the polymer support. Various prior art polymers used in such synthesis have proven inadequate for reasons such as: (1) slow diffusion rates of activated nucleotides into the support; (2) excessive swelling of various macroporous, low cross-linked support polymers; and (3) irreversible absorption of reagent onto the polymer. See for example, V. Amarnath and A. D. Broom, *Chemical Reviews* 77, 183–217 (1977).

Modified inorganic polymers are known in the prior art, primarily for use as absorption materials, for example, in liquid chromatography. The attachment of nucleosidephosphates to silica gel using a trityl linking group is described in the prior art (H. Koster, *Tetrahedron Letters*, 1527–1530, 1972) but the method is apparently applicable only to pyrimidine nucleosides. The cleavage of the nucleoside from the silica support can only be accomplished with acid to which the purine nucleosides are sensitive.

The production of phosphotriester derivatives of oligothymidylates is described in literature (R. L. Letsinger and W. B. Lunsford, *Journal of the American Chemical Society*, 98:12, 3655–3661) by reaction of a phosphorodichloridite with a 5′-O blocked thymidine and subsequent reaction of the product with a 3′-O blocked thymidine followed by oxidation of the resulting phosphite to a phosphate and removal of blocking groups to obtain the phosphotriesters; using this procedure, the tetramer and pentamer products, dTpTpTpT and dTpTpTpTpT in which T is thymidine were prepared. Unfortunately, the process requires separation and purification of products at each stage to ensure proper sequencing of the added nucleosides. Separation techniques including precipitation and washing of precipitates are necessary to implement each successive stage reaction.

In the aforementioned commonly assigned patent application are described methods for forming internucleotide bonds, i.e. bonds linking nucleosides in an oligonucleotide or polynucleotide, by reaction of halophosphoridites with suitably blocked nucleoside or oligonucleotide molecules.

The deoxynucleoside-modified silica gel is condensed with a selected nucleotide through formation of a triester phosphite linkage between the 5′-OH of the deoxynucleoside. The phosphite linkage can be produced by first incorporating the phosphite group onto the 5′-OH of the nucleoside on the silica gel followed by condensation with the added nucleoside through the 3′-OH. Alternatively, and preferably, the phosphite group is incorporated into the added nucleoside at the 3′-OH (the 5′-OH being blocked as by tritylating) and the resulting nucleoside phosphite then reacted with the 5′-OH of the nucleoside of the silica gel.

The deoxynucleoside-modified silica gel can also be condensed with a selected nucleoside through formation of a triester phosphite linkage between the 3′-OH of the deoxynucleoside of the silica gel and the 5′-OH of the selected deoxynucleoside. The phosphite linkage can be produced by first incorporating the phosphite group onto the 3′-OH of the nucleoside on the silica gel followed by condensation with the added nucleoside through the 5′-OH. Alternatively and preferably by this approach, the phosphite group is incorporated into the added nucleoside at the 5′-OH (3′-OH being blocked as by tritylating using art form procedures) and the resulting nucleoside phosphite then reacted with the 3′-OH of the nucleoside on the silica gel.

The general reaction can be represented by the following:

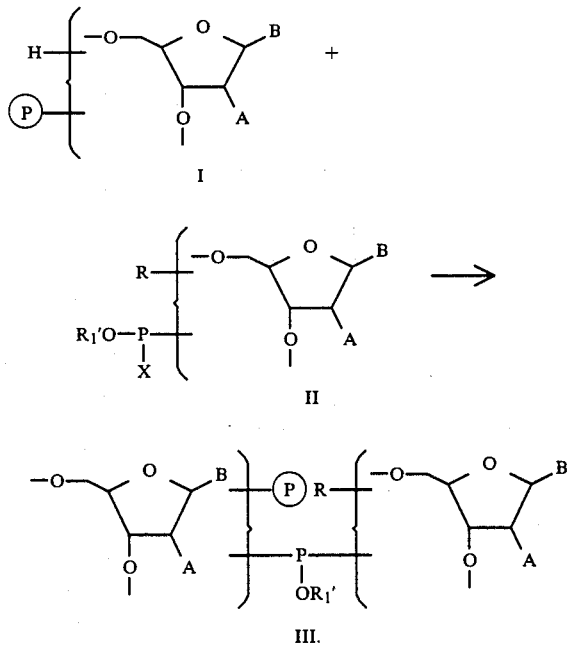

The preferred reaction is represented as follows:

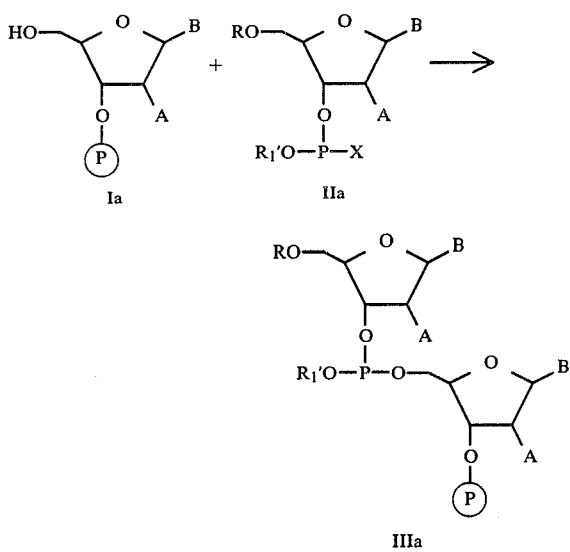

wherein Ⓟ is an inorganic polymer linked to the 3' or 5'—O— of of the nucleoside through a base hydrolyzable covalent bond; R is H or a blocking group; R'₁ is a hydrocarbyl radical containing up to 10 carbons; each B is a nucleoside or deoxynucleoside base; and each A is H, OH or OR₄ in which R₄ is a blocking group; and X is halogen, preferably Cl or Br or a secondary amino group.

The compounds of structure II and IIa wherein X is a 2° amino group include those in which the amino group is an unsaturated nitrogen heterocycle such as tetrazole, indole, imidazole, benzimidazole and similar nitrogen heterocycles characterized by at least two ethylenic double bonds, normally conjugated, and which may also include other heteroatoms such as N, S or O. These compounds of structure II and IIa wherein X is such a heterocyclic amine, i.e., one in which the amino nitrogen is a ring heteroatom, are characterized by an extremely high reactivity, and consequently relatively low stability, particularly in the indicated preparation of compounds of structure III and IIIa. These phosphoramidites and the corresponding chloridites from which they are prepared are unstable to water (hydrolysis) and air (oxidation). As a consequence, such compounds can only be maintained under inert atmosphere, usually in sealed containers, at extremely low temperatures generally well below 0° C. Thus, the use of these compounds in the preparation of compounds of structure III and IIIa requires extreme precautions and careful handling due to the aforesaid high reactivity and low stability.

The present new compounds are of structure II and IIa wherein X is a certain type of secondary amino group. Specifically, the present new compounds are those in which X is a saturated secondary amino group, i.e. one in which no double bond is present in the secondary amino radical. More particularly, X is NR'₂R'₃, wherein R'₂ and R'₃ taken separately each represents alkyl, aralkyl, cycloalkyl and cycloalkylalkyl containing up to 10 carbon atoms, R'₂ and R'₃ when taken together form an alkylene chain containing up to 5 carbon atoms in the principal chain and a total of up to 10 carbon atoms with both terminal valence bonds of said chain being attached to the nitrogen atom to which R'₂ and R'₃ are attached; and R'₂ and R'₃ when taken together with the nitrogen atom to which they are attached form a saturated nitrogen heterocycle including at least one additional heteroatom from the group consisting of nitrogen, oxygen and sulfur.

The present new compounds are not as reactive as those of the aforesaid copending application and not as unstable. However, the present new compounds do react readily with unblocked 3'-OH or 5'-OH of nucleosides under normal conditions. The present new phosphoramidites are stable under normal laboratory conditions to hydrolysis and air oxidation, and are stored as dry, stable powders. Therefore, the present new phosphoramidites are more efficiently employed in the process of forming internucleotide bonds, particularly in automated processing for formation of oligonucleotides and polynucleotides as described in the aforesaid copending application.

Amines from which the group NR₂R₃ can be derived include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methycyclohexylmethylamine, butylcyclohexylamine, morpholine, thiomorpholine, pyrrolidine, piperidine, 2,6-dimethylpiperidine, piperazine and similar saturated monocyclic nitrogen heterocycles.

The nucleoside and deoxynucleoside bases represented by B in the above formulae are well-known and include purine derivatives, e.g. adenine, hypoxanthine and guanine, and pyrimidine derivatives, e.g. cytosine, uracil and thymine.

The blocking groups represented by R₄ in the above formulae include trityl, methoxytrityl, dimethoxytrityl, dialkylphosphite, pivalyl, isobutyloxycarbonyl, t-butyl dimethylsilyl, acetyl and similar such blocking groups.

The hydrocarbyl radicals represented by R₁ include a wide variety including alkyl, alkenyl, aryl, aralkyl and cycloalkyl containing up to about 10 carbon atoms. Representative radicals are methyl, butyl, hexyl, phenethyl, benzyl, cyclohexyl, phenyl, naphthyl, allyl and cyclobutyl. Of these the preferred are lower alkyl, especially methyl and ethyl.

DESCRIPTION OF THE PREFERRED EMBODIMENTS

The preferred new compounds are those of structure IIa wherein X is di-lower alkyl amino, pyrrolidino, morpholino or piperidino, particularly preferred being the lower alkyl amino, especially, morpholino, dimethylamino and diethylamino; A is H; R'₁ is lower alkyl; R is a trityl group; B is a nucleoside or deoxynucleotide base; and Ⓟ is silica gel.

The new compounds of the present invention can be prepared according to art-recognized procedures such as by reaction of the selected secondary amine with the corresponding nucleoside phosphomonochloridite. This reaction is accomplished by dissolving the said nucleoside in an organic solvent, such as tetrahydrofuran or acetonitrile, and adding the selected secondary amine. After removing unwanted hydrochloride salt, the organic solvent solution of the phosphoramidite may be used as such for polynucleotide synthesis or the product can be isolated from the organic solvent solution and purified before further reaction.

As a further embodiment of the invention, the phosphoramidites are preferably prepared by forming the desired chloro-(2° amino)alkoxyphosphine and thereafter condensing this product with the selected nucleoside. This procedure obviates the difficulties of handling inherent in the case of the nucleoside phosphomonochlorodite which is susceptible to moisture hydrolysis and air degradation.

The reaction of the chloro-(2° amino)alkoxyphosphine is effected in an organic solvent solution of the selected nucleoside, preferably in the presence of a tertiary amine to take up the hydrogen chloride formed in the condensation reaction. The reaction proceeds smoothly at room temperature in a dry atmosphere and under an inert gas such as $N_2$ or helium. Organic solvents useful for this reaction include any solvent which will dissolve the reactants such as diethyl ether, chloroform, methylene chloride, ethylene chloride, ethyl acetate, and the like. The solution of product is separated from the precipitated hydrochloride salt of the added tertiary amine and can be used as such in forming polynucleotide or alternatively can be separated from the solvent and purified as by crystallization before further use. While the foregoing disclosure has mentioned the use of chloro compounds, it should be understood that bromo compounds can be used as desired with essentially the same results.

When the present new compounds are used in forming internucleotide bonds, they are preferably employed with proton donors. Thus, the phosphoramidites are activated by acidic compounds through protonation which facilitates the desired internucleotide bond formation. The acidic compounds to be employed for the purpose of the said activation are preferably mildly acidic and include, for example, amine hydrohalide salts and nitrogen heterocyclic compounds such as tetrazoles, imidazoles, nitroimidazoles, benzimidazoles and similar nitrogen heterocyclic proton donors. The amine hydrohalide salts to be used for the protonation activation are preferably tertiary amine salts, and, preferably, the hydrochloride salts, although hydrobromide, hydroiodide or hydrofluoride salts can also be used. The aforesaid tertiary amines include, for example, dimethylaniline, diisopropylaniline, methylethylaniline, methyldiphenylamine, pyridine and similar tertiary amines.

When the nucleoside is guanosine, i.e. where B is guanine, the use of amine hydrochlorides is not very effective for the purpose of activation, i.e. by protonation. With those compounds in which B is guanine, activation is preferably accomplished with the aforesaid nitrogen heterocyclic hydrogen donors.

Of course, as described in the aforesaid copending application, once the internucleotide bond is formed, the product is then further treated to remove blocking groups, e.g. blocking group R, which permits reaction with a further nucleoside of formula II herein and repeat reaction gives rise to the polynucleotide of determined sequence of nucleotides attached to the silica gel through the covalently-bonded linking groups, e.g. ester linking group.

After each nucleoside is added, the phosphite group preferably should be oxidized to phosphate, usually by reaction with iodine as oxidizing agent, although this can be accomplished by reaction with peroxides such as tertiary butyl peroxide and benzoyl peroxide, as well as hydroperoxides.

The oligonucleotide can then be obtained by hydrolytic cleavage to separate from the silica gel support, usually after removal of blocking groups such as R blocking groups and blocking groups on the nucleoside base moieties as described in the aforesaid copending application, generally by hydrolysis with ammonia.

Of particular value as blocking groups definitive of R are arylmethyl groups, including monoaryl dialkymethyl, diaryl monoalkylmethyl and triarylmethyl blocking groups. Of these, the preferred are the triarylmethyl of which the trityl blocking groups are well known. The triarylmethyl blocking groups are generally readily removable but they also afford a method of monitoring the sequencing of oligonucleotides as well as the yield of product obtained. One major criticism of known oligonucleotide synthesis is the lack of monitoring of the product produced in successive condensations of nucleotides. Such monitoring would require removal of an aliquot of the reaction system, e.g. the silica gel or other support on which the oligonucleotide is being synthesized, hydrolysis of the product from the support and finally analysis of the product, all of which is time-consuming. Because of this difficulty, oligonucleotides are usually synthesized without appropriate monitoring steps which is most undesirable. The use of triarylmethyl blocking groups provides a simple but accurate method of monitoring the sequence of nucleosides in the oligonucleotide product as formed, as well as the yield of product obtained at each stepwise addition of nucleoside.

This method is predicated on color formation by the triarylmethyl cation in the presence of an acid, whether a Lewis acid or a protic acid. By selection of appropriate triarylmethyl blocking groups for the phosphoramidite compound of structures II or IIa herein, which provide distinguishing color in acids, each nucleoside can be labelled with the triarylmethyl group of distinguishing color. As each condensation reaction is completed to form the phosphorus linkage illustrated in compounds of formula III and IIIa herein, the next step in the synthesis is the removal of the blocking group R therefrom. This is conveniently accomplished with a Lewis acid such as zinc bromide and simultaneously produces a color reaction, e.g. di-p-anisylphenylmethyl group forms an orange color with $ZnBr_2$, when removed from the oligonucleotide. The color can be used to identify the triarylmethyl blocking group used to identify the initial phosphoramidite employed and also to measure the extent of reaction by measurement of the intensity thereof.

Most triarylmethyl groups, in present experience, have shown color production on exposure to acids. In fact, a wide variety of colors has been obtained by varying the make-up of the triarylmethyl group, including as the aryl group not only phenyl and naphthyl but also substituted phenyl and naphthyl, as well as heterocyclic rings such as quinolinyl, furyl, thienyl, and other nitrogen, sulfur and/or oxygen containing heterocyclic rings. The said aryl groups can include substituents such as halide (F, Cl, Br, I); nitro, alkoxy, alkyl, aryl, aralkyl, cycloalkyl and like hydrocarbyl substituents. In these substituents, the number of carbon atoms should preferably be from 1 to about 12.

The preferred triarylmethyl groups are represented by the formula:

$$R_2-\underset{R_3}{\underset{|}{\overset{R_1}{\overset{|}{C}}}}-$$

wherein each of $R_1$, $R_2$ and $R_3$ is an aryl group such as phenyl, naphthyl, quinolyl, furyl, thienyl, or other nitrogen, sulfur and/or oxygen-containing heterocyclic ring; or such aryl groups with a monosubstituent such as halide (F, Cl, Br or I), nitro, lower alkoxy, lower alkyl, and aryl, aralkyl and cycloalkyl containing up to 10 carbon atoms. $R_2$ and $R_3$ each may also be alkyl, cycloalkyl or aralkyl containing up to 10 carbon atoms.

Preferable triarylmethyl groups are given in Table I:

TABLE I

LEGEND $$R_2-\underset{R_3}{\underset{|}{\overset{R_1}{\overset{|}{C}}}}-$$

Aryl Functional Groups as Defined

TABLE I-continued

LEGEND $$R_2-\underset{R_3}{\underset{|}{\overset{R_1}{\overset{|}{C}}}}-$$

| in the Legend | Color |
|---|---|
| $R_1 = R_2 = c; R_3 = a$ | Orange |
| $R_1 = c; R_2 = b; R_3 = a$ | Red |
| $R_1 = c; R_2 = d; R_3 = a$ | Orange |
| $R_1 = c; R_2 = q; R_3 = a$ | Colorless |
| $R_1 = c; R_2 = r; R_3 = a$ | Colorless |
| $R_1 = c; R_2 = p; R_3 = a$ | Red-Orange |
| $R_1 = R_2 = b; R_3 = a$ | Black |
| $R_1 = R_2 = q; R_3 = a$ | Colorless |
| $R_1 = R_2 = r; R_3 = a$ | Colorless |
| $R_1 = R_2 = p; R_3 = a$ | Violet-Red |
| $R_1 = R_2 = a; R_3 = c$ | Yellow-Orange |
| $R_1 = R_2 = a; R_3 = b$ | Yellow |
| $R_1 = R_2 = a; R_3 = d$ | Yellow |
| $R_1 = R_2 = a; R_3 = q$ | Colorless |
| $R_1 = R_2 = a; R_3 = r$ | Colorless |
| $R_1 = R_2 = c; R_3 = n$ | Violet |
| $R_1 = R_2 = b; R_3 = n$ | Blue |
| $R_1 = R_2 = p; R_3 = n$ | Deep Purple |
| $R_1 = R_2 = c; R_3 = o$ | Burnt Orange |
| $R_1 = R_2 = c; R_3 = p$ | Purple |
| $R_1 = R_2 = b; R_3 = p$ | Purple |
| $R_1 = R_2 = g; R_3 = m$ | Yellow-Orange |
| $R_1 = R_2 = f; R_3 = m$ | Colorless |
| $R_1 = R_2 = p; R_3 = m$ | Peach |
| $R_1 = R_2 = e; R_3 = m$ | Yellow |
| $R_1 = R_2 = d; R_3 = m$ | Yellow |
| $R_1 = R_2 = c; R_3 = m$ | Yellow |
| $R_1 = R_2 = a; R_3 = m$ | Colorless |
| $R_1 = R_2 = b; R_3 = m$ | Lilac |
| $R_1 = R_2 = g; R_3 = c$ | Red-Orange |
| $R_1 = R_2 = f; R_3 = c$ | Yellow |
| $R_1 = R_2 = p; R_3 = c$ | Red |
| $R_1 = R_2 = e; R_3 = c$ | Red-Orange |
| $R_1 = R_2 = d; R_3 = c$ | Red |
| $R_1 = R_2 = R_3 = c$ | Red |
| $R_1 = g; R_2 = a; R_3 = i$ | Deep Red |
| $R_1 = f; R_2 = a; R_3 = i$ | Yellow |
| $R_1 = p; R_2 = a; R_3 = i$ | Yellow |
| $R_1 = e; R_2 = a; R_3 = i$ | Red Violet |
| $R_1 = d; R_2 = a; R_3 = i$ | Burnt-Orange |
| $R_1 = c; R_2 = a; R_3 = i$ | Deep Purple |
| $R_1 = R_2 = a; R_3 = i$ | Red-Violet |
| $R_1 = b; R_2 = a; R_3 = i$ | Red |
| $R_1 = g; R_2 = a; R_3 = j$ | Yellow |
| $R_1 = f; R_2 = a; R_3 = j$ | Yellow |
| $R_1 = p; R_2 = a; R_3 = j$ | Colorless |
| $R_1 = e; R_2 = a; R_3 = j$ | Orange |
| $R_1 = d; R_2 = a; R_3 = j$ | Carmine |
| $R_1 = c; R_2 = a; R_3 = j$ | Deep Burnt Orange |
| $R_1 = R_2 = a; R_3 = j$ | Yellow |
| $R_1 = R_2 = g; R_3 = k$ | Yellow |
| $R_1 = R_2 = f; R_3 = k$ | Yellow |
| $R_1 = R_2 = p; R_3 = k$ | Colorless |
| $R_1 = R_2 = e; R_3 = k$ | Yellow-Orange |
| $R_1 = R_2 = d; R_3 = k$ | Yellow |
| $R_1 = R_2 = c; R_3 = k$ | Orange |
| $R_1 = R_2 = a; R_3 = k$ | Yellow |
| $R_1 = g; R_2 = R_3 = a$ | Yellow |
| $R_1 = f; R_2 = R_3 = a$ | Yellow |
| $R_1 = p; R_2 = R_3 = a$ | Yellow |
| $R_1 = e; R_2 = R_3 = a$ | Orange |
| $R_1 = R_2 = R_3 = a$ | Yellow |
| $R_1 = n; R_2 = l; R_3 = a$ | Green |
| $R_1 = h; R_2 = l; R_3 = a$ | Canary Yellow |
| $R_1 = g; R_2 = l; R_3 = a$ | Yellow |
| $R_1 = c; R_2 = l; R_3 = a$ | Yellow Orange |
| $R_1 = n; R_2 = g; R_3 = a$ | Green |
| $R_1 = h; R_2 = g; R_3 = a$ | Canary Yellow |
| $R_1 = R_2 = g; R_3 = a$ | Yellow |
| $R_1 = c; R_1 = g; R_3 = a$ | Yellow-Orange |
| $R_1 = b; R_2 = g; R_3 = a$ | Yellow |
| $R_1 = n; R_2 = R_3 = g$ | Green |
| $R_1 = h; R_2 = R_3 = g$ | Canary Yellow |
| $R_1 = R_2 = R_3 = g$ | Yellow |
| $R_1 = b; R_2 = R_3 = g$ | Yellow |

TABLE I-continued

LEGEND

R₂—C—
with R₁ above and R₃ below

| | |
|---|---|
| $R_1 = n$; $R_2 = j$; $R_3 = a$ | Green |
| $R_1 = h$; $R_2 = j$; $R_3 = a$ | Canary Yellow |
| $R_1 = g$; $R_2 = j$; $R_3 = a$ | Yellow |
| $R_1 = c$; $R_2 = j$; $R_3 = a$ | Yellow-Orange |
| $R_1 = n$; $R_2 = R_3 = a$ | Green |
| $R_1 = h$; $R_2 = R_3 = a$ | Yellow |
| $R_1 = a$; $R_2 = e$; $R_3 = n$ | Green |
| $R_1 = a$; $R_2 = e$; $R_3 = h$ | Yellow |
| $R_1 = a$; $R_2 = e$; $R_3 = g$ | Yellow |
| $R_1 = a$; $R_2 = e$; $R_3 = c$ | Yellow-Orange |
| $R_1 = a$; $R_2 = c$; $R_3 = n$ | Red |

All colors were determined by the following procedure: an aliquot of the hydrolyzed Grignard reaction product (the triarylmethyl alcohol produced by the procedure described in Example V herein) was analyzed by thin layer chromatography. The thin layer plates were then exposed to hydrochloric acid vapor and the color of the trityl cations recorded.

Thus, of the blocking groups definitive of R, the preferred are the arylmethyl groups, particularly triarylmethyl groups, and especially those arylmethyl groups which provide a visible color when contacted with acids.

As used herein the symbols for nucleotides and polynucleotides and polydeoxynucleotides are according to the IUPAC-IUB Commissioner of Biochemical Nomenclature Recommendations [(1970) *Biochemistry* 9, 4022].

The following examples further illustrate the invention.

EXAMPLE I

Preparation of phosphoramidites of the formula:

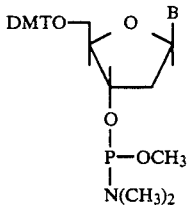

represented as compounds I–IV, in which in compound
I, B=1-Thyminyl;
II, B=1-(N-4-benzoylcytosinyl);
III, B=9-(N-6-benzoyladeninyl);
IV, B=9-(N-2-isobutyrylguaninyl);
and DMT=di-p-anisylphenylmethyl.

The synthesis of compounds I–IV begins with the preparation of chloro-N, N-dimethylaminomethoxyphosphine [CH₃O P(Cl) N(CH₃)₂] which is used as a monofunctional phosphitylating agent. A 250 ml addition funnel was charged with 100 ml of precooled anhydrous ether (−78° C.) and precooled (−78° C.) anhydrous dimethylamine (45.9 g, 1.02 mol). The addition funnel was wrapped with aluminum foil containing dry ice in order to avoid evaporation of dimethylamine. This solution was added dropwise at −15° C. (ice-acetone bath) over 2 h to a mechanically stirred solution of methoxydichlorophosphine (47.7 ml, 67.32 g, 0.51 mol) in 300 ml of anhydrous ether. The addition funnel was removed and the 1.1, three-necked round bottom flask was stoppered with serum caps tightened with copper wire. The suspension was mechanically stirred for 2 h at room temperature, then filtered and the amine hydrochloride salt washed with 500 ml anhydrous ether. The combined filtrate and washings were distilled at atmospheric pressure and the residue distilled under reduced pressure. The product was distilled at 40°–42° C. 13 mm Hg and was isolated in 71% yield (51.1 g, 0.36 mol). $d^{25} = 1.115$ g/ml. $^{31}$P-N.M.R., = −179.5 ppm (CDCl₃) with respect to internal 5% v/v aqueous H₃PO₄ standard. $^1$H-N.M.R. doublet at 3.8 and 3.6 ppm $J_{P-H} = 14$ Hz (3H, OCH₃) and two singlets at 2.8 and 2.6 ppm (6H, N(CH₃)₂). The mass spectrum showed a parent peak at m/e=141.

The 4′-O-di-p-anisylphenylmethyl nucleoside (1 mmol) was dissolved in 3 ml of dry, acid free chloroform and diisopropylethylamine (4 mmol) in a 10 ml reaction vessel preflushed with dry nitrogen. [CH₃OP(Cl)N(CH₃)₂] (2 mmol) was added dropwise (30–60 sec) by syringe to the solution under nitrogen at room temperature. After 15 min the solution was transferred with 35 ml of ethyl acetate into a 125 ml separatory funnel. The solution was extracted four times with an aqueous, saturated solution of NaCl (80 ml). The organic phase was dried over anhydrous Na₂SO₄ and evaporated to a foam under reduced pressure. The foam was dissolved with toluene (10 ml)(IV was dissolved with 10 ml of ethyl acetate) and the solution was added dropwise to 50 ml of cold hexanes (−78° C.) with vigorus stirring. The cold suspension was filtered and the white powder was washed with 75 ml of cold hexanes (−78° C.). The white powder was dried under reduced pressure and stored under nitrogen. Isolated yields of compounds I–IV were 90–94% (see Table II). The purity of the products was checked by $^{31}$P-N.M.R. Additionally, when analyzed by $^{31}$P-N.M.R., these compounds were stable for at least a month when stored at room temperature under nitrogen. Furthermore, no significant amount of (3′-3′)dinucleoside phosphite was detected by $^{31}$P-N.M.R. (less than 4%). The low content of the (3′-3′) dinucleoside phosphite represents a significant improvement over the prior art phosphite coupling procedure where a considerable amount of unwanted (3′-3′) dinucleoside phosphite was unavoidable.

The aminophosphoramidites I–IV were employed in condensation with 3′-O-blocked nucleosides to form internucleotide bonds. The phosphoramidites were activated by weak acids such as amine hydrochloride salts or tetrazoles.

A. In the following procedure, the process was monitored using $^{31}$P-N.M.R. In a 10 mm. N.M.R. tube, 1.2 molar equivalents of 3′-O-levulinylthymidine and collidine were added to a mixture formed by adding N,Ndimethylaniline hydrochloride (1 mmol) in 0.5 ml dry CDCl₃ at room temperature under N₂ to amidite compound I (0.5 mmol, −147.7 and −146.8 ppm) in 2 ml of dry, acid free CDCl₃ and an essentially quantitative yield of dinucleoside phosphite Ia (−140.8 and −139.9 ppm) was obtained.

B. Amidite compound I (0.5 mmol) and 3′-O-levulinylthymidine (0.6 mmol) were placed in a 10 mm N.M.R. tube and sublimed 1H-tetrazole (1.5 mmol) in 2.5 ml of dry acetonitrile-d₃ was added under nitrogen atmosphere. The $^{31}$P-N.M.R. spectrum was immediately recorded and displayed a quantitative yield of Ia.

Similarly, dinucleosides were obtained when II, III and IV were reacted with 3'-levulinylthymidine to form IIa, IIIa and IVa as shown in Table II. The appropriate chemical shifts of compounds I–IV and Ia–IVa with respect to internal 5% v/v aqueous $H_3PO_4$ standard are reported in Table I.

TABLE II

| COMPOUND | $\delta$-$^{31}P$ (ppm) (Acetone-$d_6$) | $\delta$-$^{31}P$ (ppm) ($CDCl_3$) | ISOLATED YIELD (%) |
|---|---|---|---|
| I | −146.0, −145.4 | −147.7, −146.8 | 93, 95* |
| II | −146.3, −145.5 | −148.0, −147.0 | 92, 95* |
| III | −146.1, −145.8 | −147.4, −147.3 | 90, 98* |
| IV | −145.9, −145.7 | −147.7, −147.2 | 90, 98* |
| Ia | −139.6, −138.9 | −140.8, −139.9 | 97** |
| IIa | −139.6, −139.0 | −140.6, −140.0 | 94** |
| IIIa | −139.7, −138.9 | −141.0, −139.9 | 97** |
| IVa | −140.3, −140.2 | −143.6, −141.9 | 93** |

*Estimated purity from $^{31}P$-N.M.R.
**Estimated yield from $^{31}P$-N.M.R.

EXAMPLE II

Alternate procedure for Chloro-N,N-disubstituted Aminomethoxyphosphine

A 50 ml dropping funnel was charged with 31.59 g of N, N-Dimethylaminotrimethylsilane (42.1 ml, 0.27 mol) which wad added dropwise over 1 h under nitrogen atmosphere to 25 ml of cold (−15° C.) methoxydichlorophosphine (35.15 g, 0.27 mol) in a 250 ml round bottom flask. A white unidentified precipitate formed during the course of the addition. Once the addition was finished, the ice-acetone bath was removed and the suspension was stirred at room temperature for 1 h. The reaction mixture was then slowly vacuum distilled through a one foot long, vacuum jacketed glass helices (3/32") column. The product distilled at 40°–42° C. 13 mm Hg and was isolated in 81% yield (30.77 g, 0.22 mol). $d^{25}$=1.115 g/ml. $^{31}P$-N.M.R.,=−179.5 ppm ($CDCl_3$) with respect to internal 5% aqueous $H_3PO_4$ standard. $^1H$-N.M.R. doublet at 3.8 and 3.6 ppm $J^P$-4=14 Hz (3H, $OCH_3$) and two singlets at 2.8 and 2.6 ppm (6H, $N(CH_3)_2$. The mass spectrum showed a parent peak at m/e=141. Anal. calcd. for $C_3H_9ClNOP$: C, 24.45; H, 6.42; N, 9.90; O, 11.30; P, 21.88. Found C, 24.53; H, 6.20; N, 10.04; O, 11.08; P, 21.44.

The procedure was successfully applied to the preparation of chloro-N, N-diethylaminomethoxyphosphine and chloropyrrolidino-methoxyphosphine.

EXAMPLE III

The applicability of phosphoramidites I–IV to the synthesis of deoxyoligonucleotides on polymer supports was accomplished by condensing compounds I–IV with N-2-isobutyryldeoxyguanosine attached covalently to silica gel. Thus, N-2-isobutyryldeoxyguanosine (1 μmole) covalently attached to silica gel (20 mg) at the 3'-position, I (10 μmole), and 1H-tetrazole (50 μmole in 0.1 ml dry acetonitrile) were shaken for 20 min and the reaction was then quenched with aqueous lutidine. The same reaction sequence was effected with II, III and IV. After the usual oxidation and deprotection procedures, d(TpG), d(CpG), d(ApG) and d(GpG) were obtained in 100%, 98%, 94%, and 93% yield respectively (measured spectrometrically from the dimethoxytrityl cation using an extinction of $7\times10^4$ at 498 nm). These dinucleotides were completely degraded by snake venom phosphodiesterase and the appropriate nucleosides and nucleotides were obtained in the proper ratios (monitored via high pressure liquid chromatography analysis of snake venom phosphodiesterase hydrolysates).

The following deoxynucleotides have been synthesized using this procedure:

d(C—T—C—A—A—A—T—G—G—G—T—C)
d(A—A—A—T—G—C—G—A—C—C—C—A)
d(T—T—T—G—A—G—C—C—A—A—C—A)
d(T—C—A—T—C—C—T—G—T—T—G—G)
d(G—G—G—C—C—G—A—A—T—T—G—T)
d(C—G—G—C—C—C—C—T—T—A—C—T)
d(T—C—C—T—C—A—A—G—T—A—A—G)
d(T—G—A—G—G—A—T—A—A—A—T—T)
d(A—T—G—T—G—T—G—A—T—T—T—A)
d(G—T—G—G—T—A—A—A—T—C—A)
d(C—C—A—C—A—A—C—C—C)
d(A—G—C—T—A—T—G—G—G—T—T—T)
d(T—T—A—G—C—T—C—A—C—T—C—A)
d(T—T—A—G—G—C—A—C—C—C)
d(C—A—G—G—C—T—T—T—A—C—A)
d(C—T—T—T—A—T—G—C—T—T—C)
d(C—G—G—C—T—C—G—T—A)
d(T—G—T—A—C—T—A—A—G)
d(G—A—G—G—T—T—G—T—A—T—G)
d(T—A—C—A—T—G—C—A—A)

EXAMPLE IV

5'-O-DMT-N-benzoyldeoxyadenosine [DMTrd(bzA)] (0.66 g., 1 mmole) in dry THF (3 ml) is added dropwise under an argon atmosphere to a stirred solution of the THF (3 ml) containing methyldichlorophosphite (0.113 ml, 1.2 mmole) and 2, 4, 6 trimethylpyridine (0.633 ml. 4.8 mmole) at −78° C. After 10 minutes at −78° C., the reaction solution is filtered through a sintered glass funnel and solvent is removed by concentration in vacuo. Excess methyl phosphodichloridite is removed by dissolving the resulting gum in toluene: THF (2 ml, 2:1 and re-evaporating in vacuo to a gum. This procedure is repeated several times to insured removal of the dichloridite. The nucleoside phosphomonochloridite is converted to the tetrazolide. The gum resulting from the final re-evaporation is dissolved in THF (2 ml). A solution of the selected secondary amine 0.9 mmole) in THF (2 ml) is then added dropwise with stirring at −78° C. to the nucleoside phosphomonochloridite. After 10 minutes at −78° C., the solution is transferred to a centrifuge tube, spun at low speed, and the supernatant is removed. This solution contains the activated nucleoside phosphoramidite. If not used immediately, this phosphoramidite can be placed in long term storage after precipitation by dropwise addition into dry pentane, followed by collection, drying in vacuo, and storing in sealed tubes under argon or other inert gas at room temperature, or lower temperatures, e.g. 0° C. All operations are performed under inert gas to avoid oxidation. At no time is the active agent exposed to air.

The foregoing procedure is applicable for the preparation of activated thymidine, deoxycytidine, and deoxyadenosine nucleotides. For the preparation of the activated deoxyguanosine nucleotide, the procedure is the same except for the stoichiometry. The molar ratio of 5'-O-DMT-N-isobutyryldeoxyguanosine [DMTrd(ibG)]; methyldichlorophosphite; 2, 4, 6 trimethylpyridine and tetrazole is 1:0.9:3.8:0.7. The steps necessary for addition of one nucleotide to the modified silica gel polymer support follow. The removal of the dimethoxytrityl group from the nucleotide is accomplished by exposing the modified silica gel support to 0.1 M ZnBr$_2$ in nitromethane for 15 to 30 minutes. The support is then washed initially with butanol: 2, 6 lutidine: THF (4:1:5 by volume) and finally with THF. The solvent ratio is not important since this step is used to remove potential zinc esters of nucleosides. This step could be eliminated but lower yields may result. Other Lewis acids could be substituted for ZnBr$_2$, such as BF$_3$, AlCl$_3$ and TiCl$_4$. However ZnBr$_2$ is preferred. Protic acids can also be used. However approximately 3-5% depurination of each purine by protic acids is observed even when the amount of acid is reduced to the minimum amount needed to remove the dimethoxytrityl group. The next step in the process is condensation of the protected and activated nucleotide to the nucleoside or oligonucleotide covalently bound to the support. This is accomplished by using 10-15 equivalents of the activated phosphoramidite and a reaction time of about one hour. The solvent is anhydrous THF. The next step in the process is the blocking of unreacted 5'-hydroxyl groups. This is accomplished using a solution of acetic anhydride, dimethylaminopyridine, pyridine and THF. This may also be accomplished using a 0.33 M solution of diethylmonotriazolophosphite in 2,6-lutidine/THF (1:5 by volume). The reaction time is 5 min. and is followed by a THF wash. As a further alternative, a solution of phenylisocyanate/lutidine (45:55 by volume) and a 90 minute reaction time may be used for this step. This solution is then removed from the modified silica gel by washing the support with THF and with acetonitrile. The first procedure is preferred. This step can be eliminated or other reagents that react with 5'-hydroxyl groups and are compatible with the overall chemistry can be substituted therefore. However, by including this step, the final purification of the desirable oligonucleotide is rendered much easier. This is because the complexity of the total synthetic material bound to the support is reduced considerably. The final step in each cycle is oxidation of the phosphite to the phosphate. A composition of 0.1 M I$_2$ in water/2, 6 lutidine/THF (1:1:3) is preferred, although other ratios can be used. Furthermore, other oxidizing agents such as N-chlorosuccinimide or aryl or alkyl peroxides, e.g., t-butyl peroxide, could also be used. After the addition of the appropriate activated nucleotides in any predetermined sequence, the deoxyoligonucleotide is removed from the support by base hydrolysis and blocking groups where present are also removed, either selectively i.e., stepwise, or in an overall hydrolysis treatment such as heating at 50° C. in ammonium hydroxide. When R$_1$ is a methyl group, this is removed by treatment with thiophenol prior to removing the oligonucleotide from the support.

EXAMPLE V

General method for synthesizing chlorotriarylmethanes

In the synthesis of this series of compounds there are two types of substrates for the respective Grignard reagents: (1) diaryl ketones, i.e. benzophenones, which require one equivalent of Grighard reagent; (2) esters of aryl carboxylic acids, which require two equivalents. The following will describe the former. Appropriate adjustments should be made for reactions of the latter type.

TABLE VII

A Summary of Reagents Used for Synthesizing Triarylcarbinols

| Reagent | Example | mmoles |
|---|---|---|
| aryl bromide | p-bromoanisole | 100 |
| magnesium | | 110 |
| diethyl ether | | 250 ml |
| iodine | | 2 crystals |
| diaryl ketone | 4-methoxybenzophenone | |

The magnesium, aryl bromide and ether are combined in 1000 ml round bottom flask. The iodine is added. In order to initiate the formation of the aryl magnesium bromide, it is necessary to crush the magnesium with a glass rod. [Note: grinding the magnesium in a Waring Blender also helps to get the reaction going.] Once the reaction has begun, it is allowed to reflux, with no external heating, until the ether ceases to boil. An ethereal solution of the diarylketone is added dropwise, with stirring. The reaction is allowed to proceed overnight. At this time the reaction is analyzed by thin layer chromotography (tlc) in 1:1 ether:hexane. The R$_f$ of the product will be approximately 0.7.

If the reaction is satisfactory, it is quenched with 10% (w/v) ammonium sulfate. The product is extracted four times with 300 ml of toluene. The extracts are dried over sodium sulfate and evaporated down as far as possible. The concentrated organic phase is dried in vacuo overnight. At this time the product crystallizes out. The product tritanol is collected in a funnel and washed with hexane.

The tritanol is taken up in 100 ml of toluene. 200 mmoles of acetyl chloride is added. 300 ml of hexane is added. The product is allowed to recrystallize overnight at −20° C. The crystals are collected, washed with hexane, and dried in vacuo.

In order to determine the reactivity of the trityl chloride, a small amount is quenched into water and N-butanol with toluene as solvent. The samples are analyzed via tlc using 3:1 hexane:ether. The trityl butyl ether runs at R$_f$ approximately 0.8 while the tritanol runs at R$_f$ approximately 0.4.

Using this procedure, the various alcohols described in Table I were prepared.

Several of the triarylmethylchlorides were condensed with the 5' hydroxyl of appropriately protected deoxynucleosides. These compounds are listed in Tables IV and V. The 5'-triarylmethyldeoxynucleosides were treated with protic and Lewis acids using carefully controlled conditions. The results of these studies are also recorded in Tables IV and V. These results show that several triarylmethyl groups forming different colors in acid solutions are hydrolyzed at approximately the same rapid rate in the presence of ZnBr$_2$. The rates are more variable with protic acids.

TABLE IV

The Lewis Acid Hydrolysis Rates of Triarylmethyl Groups Attached to the 5'-Hydroxyl of Deoxynucleosides[1]

| Triarylmethyl Group[2] | Deoxynucleoside[3] | t½ (sec) in ZnBr$_2$ | Color in Acid |
|---|---|---|---|
| R$_1$ = n; R$_2$ = c; R$_3$ = a | T | 60 | Green |
| R$_1$ = n; R$_2$ = e; R$_3$ = a | T | 60 | Red |
| R$_1$ = R$_2$ = c; R$_3$ = a | T | 60 | Orange |
| R$_1$ = R$_2$ = b; R$_3$ = n | T | 30 | Blue |
| R$_1$ = R$_2$ = c; R$_3$ = a | C | 45 | Orange |
| R$_1$ = R$_2$ = b; R$_3$ = n | C | 30 | Blue |
| R$_1$ = R$_2$ = b; R$_3$ = a | G | 20 | Black |
| R$_1$ = R$_2$ = c; R$_3$ = a | G | 20 | Orange |

TABLE IV-continued

The Lewis Acid Hydrolysis Rates of Triarylmethyl Groups Attached to the 5'-Hydroxyl of Deoxynucleosides[1]

| Triarylmethyl Group[2] | Deoxy-nucleoside[3] | t½ (sec) in ZnBr$_2$ | Color in Acid |
|---|---|---|---|
| $R_1$ = h; $R_2$ = $R_3$ = a | A | 45 | Yellow |
| $R_1$ = $R_2$ = c; $R_3$ = a | A | 20 | Orange |

[1]Reaction conditions were 0.08 M ZnBr$_2$ in nitromethane. Aliquots were removed from the reaction solution, quenched with ammonium acetate and analyzed visually after tlc and exposure to HCl vapors. Time points were taken at 10, 20, 30, 45, 60, 90, 120, 180, and 240 sec.
[2]The aromatic functional groups are defined in the legend to Table 1.
[3]The symbols T, C, G and A refer to the nucleosides thymidine, N—benzoyldeoxycytidine, N—isobutyrldeoxyguanosine, and N—benzoyldeoxyadenosine. The nucleoside 5'-hydroxyl was derivatized to contain the triarylmethyl group.

For the repetitive addition of mononucleotides to a growing oligonucleotide attached covalently to a polymer support, the various color coded triarylmethyl groups should preferably be hydrolyzed at approximately the same rate. Otherwise, each addition cycle must be individually monitored if completed manually or independently programmed if completed in a machine. Because the hydrolysis rates with ZnBr$_2$ are similar, the results outlined in Table IV suggest that most, if not all, of the triarylmethyl alcohols listed in Table 1 could be incorporated into synthetic procedures as color coded blocking groups.

TABLE V

The Protic Acid Hydrolysis Rates of Triarylmethyl Groups Attached to the 5'-Hydroxyl of Deoxynucleosides[1]

| Triarylmethyl Group[2] | Deoxy-nucleoside[3] | t½ (sec) in H+ | Color in Acid | Time (sec) to Complete Hydrolysis |
|---|---|---|---|---|
| $R_1$ = n; $R_2$ = c; $R_3$ = a | T | 30 | Green | 45 |
| $R_1$ = n; $R_2$ = e; $R_3$ = a | T | 180 | Red | >600 |
| $R_1$ = $R_2$ = c; $R_3$ = a | T | 0 | Orange | 30 |
| $R_1$ = $R_2$ = b; $R_3$ = n | T | 45 | Blue | 90 |
| $R_1$ = $R_2$ = c; $R_3$ = a | C | 0 | Orange | 30 |
| $R_1$ = $R_2$ = b; $R_3$ = n | C | 45 to 60 | Blue | 120 |
| $R_1$ = $R_2$ = b; $R_3$ = a | G | 15 | Black | 45 |
| $R_1$ = $R_2$ = c; $R_3$ = a | G | 0 | Orange | 30 |
| $R_1$ = h; $R_2$ = $R_3$ = a | A | 60 | Yellow | 240 |
| $R_1$ = $R_2$ = c; $R_3$ = a | A | 0 | Orange | 30 |

[1]Reaction conditions were 2% toluenesulfonic acid in chloroform:methanol (7:3). Aliquots were removed from the reaction solution, quenched with ammonium acetate and analyzed visually after tlc and exposure to HCl vapors. Time points were takenat 15, 30, 45, 60, 90, 120, 240, 300, and 600 sec.
[2]The aromatic functional groups are defined in the legend to Table 1.
[3]The symbols T, C, G and A refer to the nucleosides thymidine, N—benzoyldeoxycytidine, N—isobutyrldeoxyguanosine, and N—benzoyldeoxyadenosine. The nucleoside 5'-hydroxyl was derivatized to contain the triarylmethyl group.

TABLE VI

Table VI provides the spectral characteristics of selected triarylmethyl alcohols

| Triarylcarbinol[1] | λ Maximum(s)[2] (nanometers) | Extinction Coefficient (Molar$^{-1}$ cm$^{-1}$) |
|---|---|---|
| $R_1$ = $R_2$ = b; $R_3$ = a | 423 | 9300 |
| | 503 | 5200 |
| | 586 | 3900 |
| $R_1$ = $R_2$ = a; $R_3$ = h | 452 | 42000 |
| $R_1$ = a; $R_2$ = c; $R_3$ = n | 545 | 25000 |
| | 455 | 28000 |
| $R_1$ = $R_2$ = b; $R_3$ = N | 586 | 15500 |
| $R_1$ = a; $R_2$ = n; $R_3$ = e | 577 | 9500 |
| | 421 | 20500 |

[1]See the legend to Table 1 for a definition of the functional groups $R_1$, $R_2$ and $R_3$.
[2]All spectra were taken in a saturated ZnBr$_2$ nitromethane solution. All spectra were recorded on a Carey model 21, scanning from 350 nm to 600 nm.

Four deoxyoligonucleodiodes were synthesized using color coded deoxynucleotide phosphoramidities. The compounds were d(G-T-A-T-A-A-C-A-C), d(C-A-T-A-A-A-G-A-A-A-A-A), d(G-T-A-C-A-G-C-T-G-G-C-T) and (C-C-C-T-T-T-C-T-T-A-A-A). The 5'-hydroxyl of each deoxynucleotide was protected with a different triarylmethyl group. These groups as assigned for the synthesis of deoxyligonucleotides are listed in Table VII.

TABLE VII

| Triarylmethyl Group[1] | Deoxynucleoside | Color[2] |
|---|---|---|
| $R_1$ = $R_2$ = b; $R_3$ = n | N—benzoyldeoxycytidine | Blue |
| $R_1$ = h; $R_2$ = $R_3$ = a | N—benzoyldeoxyadenosine | Yellow |
| $R_1$ = c; $R_2$ = n; $R_3$ = a | Deoxythymidine | Red |
| $R_1$ = $R_2$ = c; $R_3$ = a | N—isobutyrldeoxyguanosine | Orange |

[1]The aromatic functional groups are defined in the legend to Table I.
[2]The color of the triarylmethyl group is observed when the 5'-triarylphenyl deoxynucleoside is exposed to either protic or Lewis acids.

Thus the 5'-triarylmethyl groups of N-benzoyldeoxyadenosine, N-benzoyldeoxycytidine, N-isobutyrldeoxyguanosine and deoxythymidine produced yellow, blue, orange and red colors respectively when exposed to either Lewis or protic acids. These triarylmethyldeoxynucleosides were synthesized as outlined in this disclosure. Conversion to the appropriate 5'-O-triarylmethyl and deoxynucleoside N,N-dimethylaminomethoxyphosphines was completed using the procedure of Example VI.

EXAMPLE VI

General synthesis of 5'-triarylmethyl deoxynucleosides 5 mmoles of N-protected deoxynucleoside or thymidine is dissolved in 50 ml of dry pyridine. The sample is evaporated to a gum in vacuo. 25 ml of dry pyridine is added. Six mmoles of triarylmethyl chloride is added. The reaction mixture is shaken overnight. The reaction is monitored in methanol:chloroform (1:9). The product has an R$_f$ of 0.5 and the unreacted deoxynucleoside has an R$_f$ of 0.2. The reaction is quenched with 5 ml of absolute methanol.

After 30 minutes the reaction mixture is concentrated to a small volume, taken up in ethyl acetate and extracted once with water. The organic phase is dried over sodium sulfate and concentrated to a gum. 10 ml of toluene is added and then evaporated.

The reaction mixture is then taken up in chloroform and applied to a silica gel column (5 cm × 20 cm) that has been equilibrated with 1% pyridine in chloroform. After the compound is loaded on the column, the column is washed with 500 ml of 1% pyridine in chloroform. The compound is eluted from the column with 3 to 6% methanol. The fractions containing the desired product are pooled, concentrated to a foam, taken up in chloroform and precipitated into hexane.

The precipitate is collected in a Buchner funnel and dried in vacuo. The average yield by weight is 85%.

The 5'-triarylmethyldeoxynucleosides carrying functional groups as outlined in Table VII were connected to chloro-N,N-dimethylaminomethoxyphosphine using the procedure of Example I. The 5'-triarylmethyldeoxynucleoside-3'-N,N-dimethylaminomethoxyphosphines were used as intermediates in deoxyoligonucleotide synthesis using the procedure of Example IV. Thus, the synthesis of d(G-T-A-T-A-A-C-T-A-C-A-C) begins with N-benzoyldeoxycytidine attached covalently to silica gel through the 3'-hydroxyl. The next step was condensation with 5'-O-p-tolyldiphenylmethyl-N-benzoyl-deoxyadenosine 3'-N,N-dimethylaminomethoxyphosphine. After acylation and oxidation, detritylation was completed using a saturated solution of $ZnBr_2$ in nitromethane:methanol (19:1). A yellow color indicating the addition of N-benzoyldeoxyadenosine was observed. The remaining nucleotides were added in a similar manner. During each detritylation step, colors were observed in the following sequential order: blue, yellow, red, blue, yellow, yellow, red, yellow, red, and orange. These were the expected colors and confirm that the correct deoxyoligonucleotide was synthesized. Purification of the deoxyoligonucleotide was by reverse phase high performance liquid chromatography and polyacrylamide gel electrophoresis. Characterization was by two dimension sequence analysis (Sanger, Donelson, Coulson, Kossel, and Fischer, *Proc. Natl. Acad. Sci. USA* 70, 1209-1213, 1973). This analysis reconfirmed that the correct deoxyoligonucleotide had been synthesized as indicated by the colorimetric results. The three remaining deoxyoligonucleotides were synthesized and characterized in the same way.

For the synthesis of the four enumerated oligodeoxynucleotides, the quantities of silica gel used and the choice of nucleoside joined to the silica gel support are summarized in Table VIII.

TABLE VIII

| Deoxyoligonucleotide | Nucleoside on Silica Gel | μmole Nucleoside/ Gram Silica Gel | Gram Silica Gel Used |
|---|---|---|---|
| d(G—T—A—T—A—A—C—T—A—C—A—C) | N—benzoyldeoxycytidine | 45 | 0.15 |
| d(C—A—T—A—A—G—A—A—A—A—A) | N—benzoyldeoxyadenosine | 40 | 0.15 |
| d(C—C—C—T—T—T—C—T—T—A—A—A) | N—benzoyldeoxyadenosine | 40 | 0.15 |
| d(G—T—A—C—A—G—C—T—G—G—C—T) | deoxythymidine | 53 | 0.15 |

Table IX summarizes physical parameters of 5'-O-triarylmethylnucleoside-3'-N,N-dimethylaminomethoxyphosphines used in the synthesis of the four enumerated oligodeoxynucleotides.

TABLE IX

| Nucleotide | M. Wt. | Phosphorus NMR Chemical Shifts (ppm)[1] | Color[2] |
|---|---|---|---|
| 5'-O—di-p-anisylphenylmethyl-N—isobutyryldeoxyguanosine-3'-N, N—dimethylaminomethoxyphosphine | 746 | 146.3, 146.1 | Orange |
| 5'-O—p-anisyl-1-naphthylphenyl-methyldeoxythymidine-3'-N,N—dimethylaminomethoxyphosphine | 659 | 146.4, 145.7 | Red |
| 5'-O—di-o-anisyl-1-napthylmethyl-N—benzoyldeoxycytidine-3'-N, N—dimethylaminomethoxyphosphine | 790 | 147.6, 145.4 | Blue |
| 5'-O—p-tolydiphenylmethyl-N—benzoyl-deoxyadenosine-3'-N, N—dimethylamino-methoxyphosphine | 718 | 146.4, 146.1 | Yellow |

[1]Spectra were recorded in $CH_3CN$ as solvent and against phosphoric acid as external standard.
[2]Color produced in either a Lewis acid or a protic acid.

For each condensation step, 120 μmoles of the 5'-O-triarylmethylnucleotide, acetonitrile, and 480 μmole tetrazole were used. The next steps were acylation with acetic anhydride, oxidation with $I_2$ and detritylation with $ZnBr_2$. After each detritylation step, the expected color corresponding to the required trityl cation was observed.

Once each synthesis was complete, the deoxyoligonucleotide was isolated by the following procedure. Each deoxyoligonucleotide covalently bound to silica gel (30 mg) was first treated with thiophenol:triethylamine:dioxane (1:1:2) for 90 minutes, washed four times with methanol and then washed once with diethylether. The silica gel was isolated by centrifugation and air dried. Each sample was next treated with t-butylamine:methanol (1:1) for 18 hours at 50° C. The supernatants obtained after centrifugation were removed and dried in vacuo. The silica gel samples were next treated with concentrated ammonium hydroxide at room temperature for three hours in order to remove the deoxyoligonucleotide from the silica gel. The supernatants were transferred to test tubes containing the residues from the t-butylamine procedure and the solutions concentrated in vacuo. Fresh concentrated ammonium hydroxide was added to the dry residues and the solutions were warmed at 50° C. for 22 hours in order to remove amino protecting groups from deoxyoligonucleotide bases. The samples were concentrated in vacuo and each sample was next dissolved in 200 μl water. Purification was by reverse phase high performance liquid chromatography. The retention times and solvent conditions are outlined in Table X. Each deoxyoligonucleotide was next treated with 80% acetic acid at room temperature for 1 hour in order to remove the triarylphenylmethyl group. After concentration in vacuo, each sample was purified by polyacrylamide gel electrophoresis and analyzed as to the correct deoxymononucleotide sequence by two dimension sequence analysis.

TABLE X

| Deoxyoligonucleotide | % Acetonitrile[1] | Retention Time[2] |
|---|---|---|
| d(G-T-A-T-A-A-C-T-A-C-A-C)[3] | 29 | 2.6 |
| | 27 | 3.8 |
| | 26 | 6.2 |
| d(C-A-T-A-A-G-A-A-A-A-A)[4] | 30 | 2.9 |
| | 28 | 3.0 |
| | 26 | 4.5 |
| d(C-C-C-T-T-T-C-T-T-A-A-A)[4] | 30 | 2.9 |
| | 26 | 4.6 |
| | 25 | 7.2 |
| | 24 | 9.8 |
| d(G-T-A-C-A-G-C-T-G-G-C-T)[5] | 29 | 2.6 |
| | 27 | 3.6 |

TABLE X-continued

| Deoxyoligonucleotide | % Acetonitrile[1] | Retention Time[2] |
|---|---|---|
| | 25 | 6.3 |

[1]The aqueous buffer contains 0.1 M triethylammonium acetate.
[2]1.2 min/k' at 2.0 ml/min.
[3]Triarylmethyl group was di-p-anisylphenylmethyl, preparative isolation was at 25% acetonitrile
[4]Triarylmethyl group was di-o-anisyl-1-napthylmethyl, preparative isolation was at 25% acetonitrile.
[5]Triarylmethyl group was di-p-anisylphenylmethyl, preparative isolation was at 24% acetonitrile.

What is claimed is:

1. A compound represented by one of the formulae:

wherein B is a nucleoside or deoxynucleoside base; A is H, OH or $OR_4$ in which $R_4$ is a blocking group; $R'_1$ is a hydrocarbyl radical containing up to 10 carbon atoms; X is $NR'_2R'_3$ wherein $R'_2$ and $R'_3$ taken separately each represents alkyl, aryl, aralkyl, cycloalkyl and cycloakylalkyl containing up to 10 carbon atoms; $R'_2$ and $R'_3$ when taken together form an alkylene chain containing up to 5 carbon atoms in the principal chain and a total of up to 10 carbon atoms with both terminal valence bonds of said chain being attached to the nitrogen atom to which $R'_2$ and $R'_3$ are attached; and $R'_2$ and $R'_3$ when taken together with the nitrogen atom to which they are attached form a saturated nitrogen heterocycle including at least one additional heteroatom from the group consisting of nitrogen, oxygen and sulfur; and R is a triarylmethyl blocking group selected from p-anisy-1-1-naphthylphenylmethyl, di-O-anisyl-1-naphthylmethyl, and p-tolyldiphenylmethyl.

2. A compound selected from the group consisting of:
5'-O-di-p-Anisylphenylmethyl-N-isobutyryl-deoxyguanosine-3'-N,N-dimethylaminomethoxyphosphine;
5'-O-p-Anisyl-1-naphthylphenylmethyldeoxythymidine-3'-N,N-dimethylaminomethxyphosphine;
5'-O-di-o-Anisyl-1-napthylmethyl-N-benzoyldeoxcytidine-3'-N,N-dimethylaminomethyoxyphosphine,
5'-O-p-Tolydiphenylmethyl-N-benzoyldeoxyadenosine-3'-N,N-dimethylaminomethyoxyphosphine;
5-O-di-p-Anisylphenylmethyl-N-isobutyryldeoxyguanosine-3'-N,N-morpholinomethoxyphosphine;
5'-O-p-Anisyl-1-naphthylphenylmethyldeoxythymidine-3'-N,N-morpholinomethoxyphosphine;
5'-O-di-o-Anisyl-1-naphthylmethyl-N-benzoyldeoxycytidine-3'-N,N-morpholinomethoxyphosphine;
5'-O-p-Tolydiphenylmethyl-N-benzoyldeoxyadenosine-3'-N,N-morpholinomethoxyphosphine;
5'-O-di-p-Anisylphenylmethyl-N-acetyldeoxyguanosine-3'-N,N-dimethylaminomethoxyphosphine;
5'-O-di-p-Anisylphenylmethyl-N-benzoyldeoxyguanosine-3'-N,N-dimethylaminomethoxyphosphine;
5'-O-di-o-Anisyl-1-naphthylmethyl-N-acetyldeoxycytidine-3'-N,N-dimethylaminomethoxyphosphine;
5'-O-di-o-Anisyl-1-naphthylmethyl-N-isobutyryldeoxycytidine-3'-N,N-dimethylaminomethoxyphosphine;
5'-O-p-Tolydiphenylmethyl-N-acetyldeoxyadenosine-3'-N,N-dimethylaminomethoxyphosphine;
5'-O-p-Tolydiphenylmethyl-N-isobutyryladenosine-3'-N,N-dimethylaminomethoxyphosphine;
5'-O-di-p-Anisylphenylmethyl-N-acetyldeoxyguansine-3'-N,N-morpholinomethoxyphosphine;
5'-O-di-p-Anisylphenylmethyl-N-benzoyl-deoxyguanosine-3'-N,N-morpholinomethoxyphosphine;
5'-O-di-o-Anisyl-1-naphthylmethyl-N-isobutyryldeoxycytidine-3'-N,N-morpholinomethoxyphosphine;
5'-O-di-o-Anisyl-1-napthylmethyl-N-acetyldeoxycytidine-3'-N,N-morpholinomethoxyphosphine;
5'O-p-Tolydiphenylmethyl-N-acetyldeoxyadenosine-3'-N,N-morpholinomethoxyphosphine; and
5'-O-p-Tolydiphenylmethyl-N-isobutyryldeoxyadenosine-3'-N,N-morpholinomethoxyphosphine.

3. The compound according to claim 2 which is 5'-O-di-p-Anisylphenylmethyl-N-isobutyryl-deoxyguanosine-3'-N,N-dimethylaminomethoxyphosphine.

4. The compound according to claim 2 which is 5'-O-p-Anisyl-1-naphthylphenylmethydeoxythymidine-3'-N,N-dimethylaminomethoxyphosphine.

5. The compound according to claim 2 which is 5'-O-di-o-Anisyl-1-naphthylmethyl-N-benzoyl-deoxcytidine-3'-N,N-dimethylaminomethyloxyphosphine.

6. The compound according to claim 2 which is 5'-O-p-Tolydiphenylmethyl-N-benzoyldenoxyadenosine-3'-N,N-dimethylaminemethoxyphosphine.

7. The compound according to claim 2 which is 5'-O-di-p-Anisylphenylmethyl-N-isobutyryldeoxyguanosine-3'-N,N-morpholinomethoxyphosphine.

8. The compound according to claim 2 which is 5'-O-p-Anisyl-1-naphthylphenylmethyldeoxythymidine-3'-N,N-morpholinomethoxyphosphine.

9. The compound according to claim 2 which is 5'-O-di-o-Anisyl-1-naphthylmethyl-N-benzoyldeoxycytidine-3'-N,N-morpholinomethoxyphosphine.

10. The compound according to claim 2 which is 5'-O-p-Tolydiphenylmethyl-N-benzoyldeoxyadenosine-3'-N,N-morpholinomethoxyphosphine.

11. The compound according to claim 2 which is 5'-O-di-p-Anisylphenylmethyl-N-acetyldeoxyguanosine-3'-N,N-dimethylaminomethoxyphosphine.

12. The compound according to claim 2 which is 5'-O-di-p-Anisylphenylmethyl-N-benzoyldeoxyguanosine-3'-N,N-dimethylaminomethoxyphosphine.

13. The compound according to claim 2 which is 5'-O-di-o-Anisyl-1-naphthylmethyl-N-acetyldeoxycytidine-3'-N,N-dimethylaminomethoxyphosphine.

14. The compound according to claim 2 which is 5'-O-di-o-Anisyl-1-naphthylmethyl-N-isobutyryldeoxycytidine-3'-N,N-dimethylaminomethoxyphosphine.

15. The compound according to claim 2 which is 5'-O-p-Tolydiphenylmethyl-N-acetyldeoxyadenosine-3'-N,N-dimethylaminomethoxyphosphine.

16. The compound according to claim 2 which is 5'-O-p-Tolydiphenylmethyl-N-isobutyryladenosine-3'-N,N-dimethylaminomethoxyphosphine.

17. The compound according to claim 2 which is 5'-O-di-p-Anisylphenylmethyl-N-acetyldeoxyguanosine-3'-N,N-morpholinomethoxyphosphine.

18. The compound according to claim 2 which is 5'-O-di-p-Anisylphenylmethyl-N-benzoyldeoxyguanosine-3'-N,N-morpholinomethoxyphosphine.

19. The compound according to claim 2 which is 5'-O-di-o-Anisyl-1-naphthylmethyl-N-isobutyryldeoxycytidine-3'-N,N-morpholinomethoxyphosphine.

20. The compound according to claim 2 which is 5'-O-di-o-Anisyl-1-napthylmethyl-N-acetyldeoxycytidine-3'-N,N-morpholinomethoxyphosphine.

21. The compound according to claim 2 which is 5'-O-p-Tolydiphenylmethyl-N-acetyldeoxyadenosine-3'-N,N-morpholinomethyphosphine.

22. The compound according to claim 2 which is 5'-O-p-Tolydiphenylmethyl-N-isobutyryldeoxyadenosine-3'-N,N-morpholinomethoxyphosphine.

23. A compound according to claim 1 wherein said triarylmethyl blocking group is p-anisyl-1-naphthylphenylmethyl.

24. A compound according to claim 1 wherein said triarylmethyl blocking group is di-O-anisyl-1-naphthylmethyl.

25. A compound according to claim 1 wherein said triarylmethyl blocking group is p-tolyldiphenylmethyl.

* * * * *